ns Patent [19]

Hoehn

[11] 4,048,184
[45] Sept. 13, 1977

[54] 6-PHENYL-2H-PYRAZOLO[3,4-B]PYRIDINES

[75] Inventor: Hans Hoehn, Tegernheim, Germany

[73] Assignee: E. R. Squibb & Sons, Inc., Princeton, N.J.

[21] Appl. No.: 741,572

[22] Filed: Nov. 15, 1976

[51] Int. Cl.² .......................................... C07D 471/04
[52] U.S. Cl. ..................... 260/296 H; 260/268 BC; 260/293.6; 260/294.8 C; 260/295 S; 424/250; 424/256; 424/267
[58] Field of Search ..................... 260/296 H, 294.8 R, 260/295 S

[56] References Cited
U.S. PATENT DOCUMENTS

| 3,828,057 | 8/1974 | Denzel et al. | 260/296 H |
| 3,855,675 | 12/1974 | Denzel et al. | 260/296 H |
| 3,985,757 | 10/1976 | Denzel et al. | 260/294.8 C |

Primary Examiner—Alan L. Rotman
Attorney, Agent, or Firm—Lawrence S. Levinson; Merle J. Smith

[57] ABSTRACT

New 6-phenyl-2H-pyrazolo[3,4-b]pyridines have the general formula

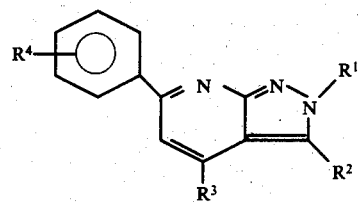

The new compounds and salts thereof are useful as anti-inflammatory agents.

9 Claims, No Drawings

6-PHENYL-2H-PYRAZOLO[3,4-B]PYRIDINES

SUMMARY OF THE INVENTION

This invention relates to new 6-phenyl-2H-pyrazolo[3,4-b]pyridines, which have the general formula (I)

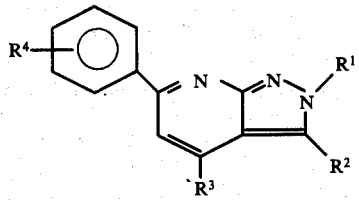

and to a method for producing them.

$R^1$ is lower alkyl, phenyl, phenyl-lower alkyl or cyclo-lower alkyl.

$R^2$ is hydrogen, lower alkyl or phenyl.

$R^3$ is lower alkoxy or a cyclic or acyclic amino group.

$R^4$ is hydrogen, halogen, hydroxy, lower alkoxy or amino.

BACKGROUND OF THE INVENTION

My prior application Ser. No. 467,048, filed May 5, 1974, together with Ernst Schulze, includes a group of 1-substituted 6-phenyl-1H-pyrazolo[3,4-b]pyridines which are produced by the reaction of 1-substituted-5-amino-pyrazoles with a benzoylacetic acid ester. The same reaction of a benzoylacetic acid ester with 2-substituted 5-aminopyrazoles unexpectedly yields 5-phenylpyrazolo[1,5-a]-pyrimidin-7(1H)ones. In order to obtain the 2-substituted 6-phenyl-2H-pyrazolo[3,4-b]pyridines of this invention, rearrangement of the pyrazolopyrimidine is required. Thus the method of ring formation of 2H-pyrazolopyridines is different from the method of producing the 1H series.

DETAILED DESCRIPTION OF THE INVENTION

The symbols have the following meanings in formula I and throughout this specification:

$R^1$ is lower alkyl, phenyl, phenyl-lower alkyl or cyclo-lower alkyl. The lower alkyl groups are straight or branched chain hydrocarbon groups having up to seven carbon atoms like methyl, ethyl, propyl, isopropyl, butyl, isobutyl, t-butyl, pentyl and the like. The $C_1$–$C_4$ lower alkyl groups and especially $C_1$–$C_2$ groups are preferred. The phenyl-lower alkyl groups include a phenyl group attached to a lower alkyl group such as those defined. Phenylmethyl and phenylethyl are representative and preferred. The cyclo-lower alkyl groups include the $C_4$–$C_7$ cycloaliphatics cyclobutyl, cyclopentyl, cyclohexyl and cycloheptyl, the $C_5$–$C_6$ members being preferred.

$R^2$ is hydrogen, lower alkyl or phenyl. The lower alkyl groups are the same as those defined above and the same members are preferred.

$R^3$ is lower alkoxy or an acyclic or cyclic amino group. The lower alkoxy group include such lower alkyl groups attached to an oxygen. They include, for example, methoxy, ethoxy, propoxy, isopropoxy and the like. The $C_1$–$C_4$ lower alkoxy groups and especially $C_1$–$C_2$ groups are preferred.

The amine group represented by $R^3$ is the group

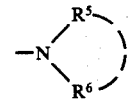

wherein $R^5$ is hydrogen or lower alkyl and $R^6$ is lower alkyl or together $R^5$ and $R^6$ join to complete an unsubstituted or substituted 5- or 6-membered heterocyclic of the group pyrrolidine, piperidine, piperazine or the substituted members (lower alkyl)piperidine, (lower alkyl)piperazine or (hydroxy-lower alkyl)piperazine.

The acyclic amine groups include, for example, lower alkylamino groups such as methylamino, ethylamino, propylamino, isopropylamino, butylamino, isobutylamino, t-butylamino and the like, di(lower alkyl)amines such as dimethylamino, diethylamino, methylethylamino, dipropylamino, dibutylamino, methylpropylamino and the like.

The heterocyclic

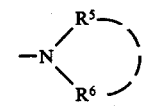

groups, in addition to the unsubstituted heterocycles include, for example, 2-, 3- or 4-methylpiperidino, 2-,3- or 4-ethylpiperidino, 2-, 3- or 4-methylpiperazino, 2-,3- or 4-ethylpiperazino, 4-(hydroxyethyl)-piperazino and the like. 4-substitution on the heterocycle is preferred.

The phenyl group in the 6-position is preferably unsubstituted but it can also be substituted, preferably in the 4-position. $R^4$ in formula I can then represent hydrogen, halogen, hydroxy, lower alkoxy or amino. The lower alkoxy groups are the same kind as described above. The halogens are the four common halogens, chlorine and bromine being preferred in that order.

Especially preferred compounds of formula I are those wherein $R^1$ is lower alkyl, especially methyl, or phenyl; $R^2$ is hydrogen; $R^3$ is lower alkoxy, lower alkylamino, di(lower alkyl)amino or piperidino; and $R^4$ is hydrogen or halogen, especially hydrogen or chloro; and acid addition salts thereof, especially the hydrochloride.

The new compounds of formula I are formed by the following series of reactions. The symbols in the structural formulas have the same meaning as previously described.

A 5-aminopyrazole of the formula

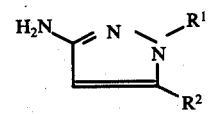

[produced analogous to the procedure described in Angew. Chem. 86, 237 (1974); Farmaco Ed. sci 16, 557–570 (1961); Brit. Pat 743 505] is made to react with a benzoylacetic acid ester of the formula (III)

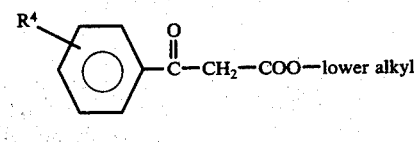

by heating at about 120°-140° C. in the presence of a phosphoric acid like polyphosphoric acid producing a compound of the formula (IV)

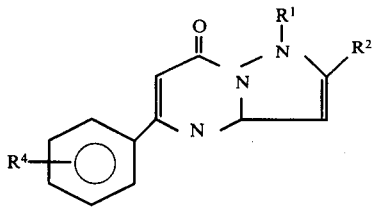

Rearrangement of the 5-phenylpyrazolo[1,5-a]pyrimidin-7(1H)-one of formula IV is effected by heating the compound of formula IV at about 250°-300° C with or without a solvent, yielding the 4-hydroxy-6-phenyl-2H-pyrazolo[3,4-b]pyridine of the formula (V)

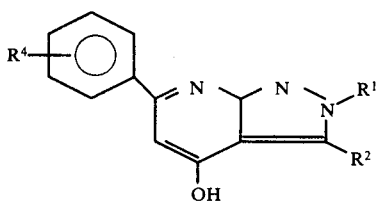

The solvents in which the rearrangement can be effected are inert high boiling organic solvents like diphenyl ether, halogenated diphenyl ethers, polychlorinated biphenyls or the like. This 4-hydroxy derivative is refluxed for several hours with a phosphorus halide like phosphorus oxychloride to give the compound of the formula (VI)

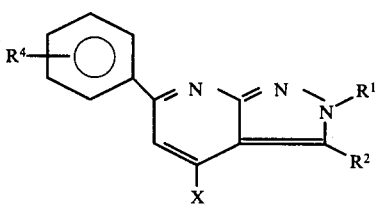

wherein X is halogen, preferably chlorine.

Reaction of the compound of formula VI with a metal alcoholate R-O-Met wherein R is lower alkyl and Met is a metal, e.g., an alkali metal like sodium or potassium yields the product of formula I wherein $R^3$ is lower alkoxy. An alcohol corresponding to the alkoxide used is preferably employed as solvent or reaction medium. When an amine

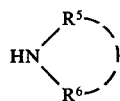

is used to react with the halogenated intermediate of formula VI the product is a compound wherein $R^3$ is an amino group corresponding to the amine VII used in the reaction. An excess of the amine reactant, when the amine is a liquid, alcohol or an organic hydrocarbon solvent like benzene, toluene or the like can be used as the reaction medium.

The compounds of formula I form salts which are also part of this invention. The salts include acid addition salts, particularly the non-toxic, physiologically acceptable members. The bases of formula I form salts by reaction with a variety of inorganic and organic acids providing acid addition salts including, for example, hydrohalides (especially hydrochloride and hydrobromide), sulfate, nitrate, borate, phosphate, fumarate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt in an appropriate medium in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention have antiinflammatory properties and are useful as antiinflammatory agents, for example, to reduce local inflammatory conditions such as those of an edematous nature or resulting from proliferation of connective tissue in various mammalian species such as rats, dogs and the like when given orally in dosages of about 5 to 100 mg/kg/day, preferably 10 to 50 mg/kg/day, in single or 2 to 4 divided doses, as indicated by the carrageenan edema assay in rats. The active substance may be utilized in compositions such as tablets, capsules, solutions or suspensions containing up to about 500 mg per unit of dosage of a compound or mixture of compounds of formula I or a physiologically acceptable acid addition salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.01 to 2 percent by weight of active substance in a lotion, salve or cream may also be used.

The following examples are illustrative of the invention and constitute preferred embodiments. They serve as models, also, for other members of the group which are produced by suitable variation of the substituents in the reactants. All temperatures are in degrees celsius.

EXAMPLE 1

2-Methyl-6-phenyl-2-H-pyrazolo[3,4-b]pyridin-4-ol a.

1-Methyl-5-phenylpyrazolo[1,5-a]pyrimidin-7(1H)-one 192.2 g. of benzoylacetic ethyl ester (1 mol.) are added dropwise to a stirred mixture of 97.1 g. of 5-amino-2-methylpyrazole (1 mol.) and 500 g. of polyphosphoric acid and heated to 120°-130°. Reaction time is maintained for 1.5 hours. After the mixture has cooled to room temperature, 2.2 liters of water are added and stirring is continued until the compound becomes crystalline. The 1-methyl-5-phenylpyrazolo[1,5-a]-pyrimidin-7-(1H)-one phosphate is washed with water and dried at 80°, yield 242 g.

The phosphate is converted to the free base by dissolving 242 g. of the compound in 900 ml. of boiling water. After the turbid solution is treated with charcoal and filtered, concentrated aqueous sodium hydroxide is added to the filtrate. The resulting oily 1-methyl-5-phenylpyrazolo[1,5-a]pyrimidin-7(1H)-one is stirred until it becomes crystalline. The collected material is washed with water and dried at 70°; m.p. 147°-148°;

yield 61 g. Recrystallization of a sample from alcohol does not elevate the melting point.

b. 2-Methyl-6-phenyl-2H-pyrazolo[3,4-b]pyridin-4-ol 152 g. of 1-methyl-5-phenylpyrazolo[1,5-a]pyrimidin-7-(1H)-one (0.67 mol.) in 500 ml. of diphenyl ether are heated at 250°, while stirring, for 90 minutes. After standing overnight, the crystallized 2-methyl-6-phenyl-2H-pyrazolo[3,4-b]pyridin-4-ol is filtered off, washed with ether and dried at 70°, yield: 146.6 g. (96%); m.p. 241°-243°. A sample recrystallized from acetonitrile melts at 242°-244°.

EXAMPLE 2

4-Chloro-2-methyl-6-phenyl-2H-pyrazolo[3,4-pyridine 39 g. of 2-methyl-6-phenyl-2H-pyrazolo[3,4-b]pyridin-4-ol (0.17 mol.) are refluxed in 195 ml. of phosphorus oxychloride for 90 minutes. The excess phosphorus oxychloride is removed in vacuo and the residue is poured onto ice. Concentrated aqueous ammonia is added under external cooling to adjust the mixture to pH 8-9. Stirring is continued for one additional hour. The collected 4-chloro-2-methyl-6-phenyl-2H-pyrazolo[3,4-b]pyridine is washed with water and dried at 70°, yield: 41 g. (100%); m.p. 177°-179°. Recrystallization from ethyl acetate gives a melting point of 189°-190°.

EXAMPLE 3

N,2-Dimethyl-6-phenyl-2H-pyrazolo[3,4-b]pyridin-4-amine, hydrochloride (1:1)

17 g. of 4-chloro-2-methyl-6-phenyl-2H-pyrazolo[3,4-b]pyridine (0.07 mol.) and 60 ml. of alcoholic methylamine (270 g/l) are heated at 150°-160° in an autoclave for four hours. After cooling to room temperature, the solution is evaporated in vacuo and the residue is extracted with chloroform. To the chloroform extract is added ethereal hydrochloric acid to give the crude hydrochloride of N,2-dimethyl-6-phenyl-2H-pyrazolo[3,4-b]pyridine which, after treatment with ether, becomes crystalline.

For purification, the hydrochloride is dissolved in water, and to the clear solution diluted aqueous ammonia is added, yielding 14.2 g. (85%) of the free N,2-dimethyl-6-phenyl-2-H-pyrazolo[3,4-b]pyridin-4-amine; m.p. 217°-219° (acetonitrile).

Alcohol is added dropwise to 12.65 g. of N,2-dimethyl-6-phenyl-2H-pyrazolo[3,4-b]pyridin-4-amine (0.053 mol.) suspended in 400 ml. of chloroform until the compound is dissolved. Then 0.064 mol. of ethereal hydrochloric acid is added. Addition of more ether precipitates the hydrochloride which contains half a mole of water in its molecule, yield: 11.2 g. (74%); m.p. 291°-292° (dec.).

EXAMPLE 4

N-Butyl-2-methyl-6-phenyl-2H-pyrazolo[3,4-b]pyridin-4-amine 12.2 g. of 4-chloro-2-methyl-6-phenyl-2H -pyrazolo[3,4-b]pyridine (0.05 mol.) and 100 ml. of butylamine are heated at 150° in an autoclave for three hours. Then the reaction mixture is evaporated in vacuo and the residue is treated with water. Filtering off, washing with water and drying gives 12.8 g. (91%) of N-butyl-2-methyl-6-phenyl-2H-pyrazolo[3,4-b]pyridin-4-amine; m.p. 160°-161° (ethyl acetate).

EXAMPLE 5

2-Methyl-N-(1-methylpropyl)-6-phenyl-2H-pyrazolo[3,4-b]-pyridin-4-amine 14.6 g. of 4-chloro-2-methyl-6-phenyl-2H-pyrazolo-[3,4-b]pyridine (0.06 mol.) and a solution of 100 ml. of methylpropylamine in 150 ml. of benzene are heated at 220° in an autoclave for 20 hours. After cooling, the mixture is evaporated in vacuo, and to the residue 100 ml. of water and 100 ml. of chloroform are added. After agitation, the chloroform extract is separated and dried with Na$_2$SO$_4$. Evaporation yields an oily product which, after treatment with ether, becomes solid. 14.3 g. of 2-methyl-N-(1-methylpropyl)-6-phenyl-2H-pyrazolo[3,4-b]pyridin-4-amine, (m.p. 148°-151°), are recrystallized from ethyl acetate giving a pure product of the melting point 156°-157°.

EXAMPLE 6

N,N-Diethyl-2-methyl-6-phenyl-2H-pyrazolo[3,4-b]pyridin-4-amine, hydrochloride (2:3), hydrate 17.1 g. of 4-chloro-2-methyl-6-phenyl-2H-pyrazolo-[3,4-b]pyridine (0.07 mol.) are added to 100 ml. of diethylamine and 150 ml. of benzene. The reaction mixture is heated at 220° for 18 hours in an autoclave. After cooling to room temperature, the precipitated diethylamine hydrochloride is filtered off and the filtrate is evaporated in vacuo to give 18.9 g. (96%) of N,N-diethyl-2-methyl-6-phenyl-2H-pyrazolo[3,4-b]pyridin-4-amine; m.p. 144°-146° (benzene).

To 9.8 g. of the amine (0.035 mol.), dissolved in 100 ml. of chloroform, 0.07 mol. (7.7 ml. 330 g. HCl/l) of ethereal hydrochloic acid are added. The precipitated hydrochloride is filtered off, washed with alcohol, recrystallized from acetonitrile containing several drops of alcoholic hydrochloric acid, and dried for four hours at 40° in vacuo, yield: 11.5 g. (82%); m.p. 166°-168° (dec.).

EXAMPLE 7

2-Methyl-6-phenyl-4-(1-piperidinyl)-2H-pyrazolo[3,4-b]pyridine, hydrochloride (1:2), dihydrate 17.1 g. of 4-chloro-2-methyl-6-phenyl-2H-pyrazolo[3,4-b]pyridine (0.07 mol.) and 130 ml. of piperidine are heated at 180° in an autoclave for 3 hours. The product is worked up as in Example 5. 2-Methyl-6-phenyl-4-(1-piperidinyl)-2H-pyrazolo[3,4-b]pyridine is recrystallized from acetonitrile, yield: 15.5 g. (76%); m.p. 163°-166°.

The hydrochloride is prepared by the procedure of Example 6 and is recrystallized from acetonitrile/ethyl acetate (1:2), yield: 86%; m.p. 121°-122° (dec.).

EXAMPLE 8

2-Methyl-4-(3-methylbutoxy)-6-phenyl-2H-pyrazolo[3,4-b]-pyridine maleinate (2:3)

To a solution of 1.61 g. of sodium (0.07 mol.) in 200 ml. of 3-methyl butanol, 17.1 g. of 4-chloro-2-methyl-6-phenyl-2-pyrazolo[3,4-b]pyridine (0.07 mol.) are added and the mixture is refluxed for six hours while stirring. The cooled solution is agitated with water, the organic layer dried and then evaporated in vacuo to give 20 g. (97% of oil. To 18.5 g. of the oil (0.063 mol.), dissolved in 50 ml. of ether, a solution of 14.6 g. of maleic acid (0.126 mol.) in 500 ml. of ether is added. The precipitated maleiate of 2-methyl-4-(3-methylbutoxy)-6-phenyl-2H-pyrazolo[3,4-b]pyridine, at first oily, crystallizes on standing overnight, yield: 24.6 g. (83%); m.p. 114°–116°. Recrystallization from ethyl acetate gives a product which melts at 119°–120°.

EXAMPLE 9

4-Ethoxy-2-methyl-6-phenyl-2H-pyrazolo[3,4-b]pyridine 8.5 g. of 4-chloro-2-methyl-6-phenyl-2H-pyrazolo[3,4-b]pyridine (0.035 mol.) are added to a solution of 0.9 g. of sodium (0.038 mol.) in 100 ml. of absolute ethanol. The mixture is heated at 150° in an autoclave for five hours. After cooling, the crystallized 4-ethoxy-2-methyl-6-phenyl-2H-pyrazolo[3,4-b]pyridine is filtered off, washed with alcohol and then with water, yield: 6.2 g.; m.p. 170°–171°. An additional crop of 2.4 g. is obtained by evaporation of the mother liquid, total yield: 8.6 g. (97%). Recrystallization from ethanol gives a product of the melting point 171°–172°.

EXAMPLE 10

6-(4-Chlorophenyl)-2-methyl-2H-pyrazolo[3,4-b]pyridin-4-ol a. 1-Methyl-5-(p-chlorophenyl)pyrazolo[1,5-a]pyrimidin-7(1H)-one Treatment of 5-amino-2-methylpyrazole with p-chlorobenzoylacetic ethyl ester in polyphosphoric acid according to the procedure of Example 1a yields 1-methyl-5-(p-chlorophenyl)pyrazolo[1,5-a]pyrimidin-7(1H)-one, yield: 68%; m.p. 215°–216°.

b. 6-(4-Chlorophenyl)-2-methyl-2H-pyrazolo[3,4-pyridin-4-ol

A mixture of 40.5 g. of 1-methyl-5-(p-chlorophenyl)-pyrazolo[1,5-a]pyrimidin-7(1H)one (0.156 ml.) and 120 ml. of diphenyl ether is heated with stirring at 250° for 90 minutes and then allowed to stand overnight. The crystallized 6-(4-chlorophenyl)-2-methyl-2H-pyrazolo[3,4-b]pyridin-4-ol is filtered off, washed with acetonitrile and dried at 80°, yield: 37.3 g. (90%); m.p. 302°–305°. A sample, recrystallized from ethanol, melts at 305°–307°.

EXAMPLE 11

4-Chloro-6-(4-chlorophenyl)-2-methyl-2H-pyrazolo[3,4-b]pyridine

Following the procedure of Example 2, 37.8 g. of 6-(4-chlorophenyl)-2-methyl-2H-pyrazolo[3,4-b]pyridin-4-ol (0.146 mol.) and 165 ml. of phosphorus oxychloride yield 35.1 g. (86%) of 4-chloro-6-(4-chlorophenyl)-2-methyl-2H-pyrazolo[3,4-b]pyridine, recrystallized from ethanol; m.p. 177°–179°.

EXAMPLE 12

6-(4-Chlorophenyl)-2-methyl-N-(1-methylpropyl)-2H-pyrazolo-[3,4-b]pyridin-4-amine 7.9 g. of 4-chloro-6-(4-chlorophenyl)-2-methyl-2H-pyrazolo[3,4-b]pyridine (0.028 mol.) and 80 ml. of 1-methylpropylamine are heated at 200° in an autoclave for 18 hours. The product is worked up according to the procedure of Example 4 to obtain 7.4 g. (84% of 6-(4-chlorophenyl)-2-methyl-N-(1-methylpropyl)-2H-pyrazolo[3,4-b]pyridin-4-amine; m.p. 208°–209° (ethyl acetate).

EXAMPLE 13

6-(4-Chlorophenyl)-N,N-diethyl-2-methyl-2H-pyrazolo[3,4-b]-pyridin-4-amine, hydrochloride (1:1)

13 g. of 4-chloro-6-(4-chlorophenyl)-2-methyl-2H-pyrazolo[3,4-b]pyridine (0.047 mol.) and 130 ml. of diethylamine are heated at 200° in an autoclave for 16 hours. The product is worked up according to the procedure of Example 4 to obtain 12.5 g. of 6-(4-chlorophenyl)-N,N-diethyl-2-methyl-2H-pyrazolo[3,4-b]pyridin-4-amine; m.p. 211°–212° (ethyl acetate).

By dissolving the amine in absolute ethanol and adding ethereal hydrochloric acid then ether precipitates the hydrochloride, yield 86%; m.p. 191°–193° (dec.) acetonitrile).

EXAMPLE 14

6-(4-Chlorophenyl)-N,2-dimethyl-2H-pyrazolo[3,4-b]pyridin-4-amine, hydrochloride (1:1)

By substituting methylamine for the diethylamine in the procedure of Example 13 and heating at 160° for four hours, 6-(4-chlorophenyl)-N,2-dimethyl-2H-pyrazolo[3,4-b]pyridine-4-amine is obtained, yield: 77%, m.p. 182°–184° (acetonitrile). The hydrochloride is prepared by the procedure of Example 13, m.p. 202°–204° (abs. ethanol); yield: 87%.

EXAMPLE 15

2,6-Diphenyl-2H-pyrazolo[3,4-b]pyridin-4-ol a. 1,5-Diphenylpyrazolo[1,5-a]pyrimidin-7(1H)-one A mixture of 10 g. of 5-amino-2-phenylpyrazole (0.063 mol.), 12.1 g. of benzoylacetic acid ethyl ester (0.063 mol.) and 50 g. of polyphosphoric acid is heated at 110°–120° with stirring for 90 minutes. After cooling, 200 ml. of water and then concentrated aqueous ammonia is added under external cooling to adjust the mixture to pH 9. The collected 1,5-diphenylpyrazolo[1,5-a]pyrimidin-7(1H)-one is washed with water and dried at 70°, yield: 17 g. (94%); m.p. 194°–200°. A sample, recrystallized from absolute ethanol, melts at 205°–207°.

b. 2,6-Diphenyl-2H-pyrazolo[3,4-b]pyridin-4-ol 6.5 g. of 1,5-diphenylpyrazolo[1,5-a]pyrimidin-7(1H)-one (0.0226 mol.) and 18 g. of diphenyl ether are heated at 250°–260° for 90 minutes. After standing overnight, the crystallized 2,6-diphenyl-2H-pyrazolo[3,4-b]pyridin-4-ol is filtered off, washed with ethanol and dried at 80°, yield: 6.1 g. (94%); m.p. 280°–281°.

EXAMPLE 16

4-Chloro-2,6-diphenyl-2H-pyrazolo[3,4-b]pyridine 5.5 g. of 2,6-diphenyl-2H-pyrazolo[3,4-b]pyridin-4-ol (0.019 mol.) and 27.5 ml. of phosphorus oxychloride are refluxed with stirring for 90 minutes. The cooled mixture is poured onto crushed ice, then made alkaline with concentrated aqueous ammonia while adding ice. The collected 4-chloro-2,6-diphenyl-2H-pyrazolo[3,4-b]pyridine is washed with water and dried at 80°; m.p. 175°–177°. A sample, recrystallized from ethanol, melts at 176°–178°; yield: 5 g. (86%).

EXAMPLE 17

N-Methyl-2,6-diphenyl-2H-pyrazolo[3,4-b]pyridin-4-amine, hydrochloride (1:1)

14 g. of chloro-2,6-diphenyl-2H-pyrazolo[3,4-b]-pyridine (0.046 mol.) and 112 ml. of methylamine in benzene (0.046 mol.) are heated at 200° in an autoclave for 18 hours. The product, N-methyl-2,6-diphenyl-2H-pyrazolo[3,4-b]-pyridine-4-amine is worked up according to the procedure of Example 4, yield: 13.1 g. (95%); m.p. 210°–212° (acetonitrile).

To 10 g. of N-methyl-2,6-diphenyl-2H-pyrazolo[3,4-b]-pyridin-4-amine (0.033 mol.), dissolved in a mixture of 250 ml. of chloroform and 150 ml. of absolute ethanol, 7.3 ml. of ethereal hydrochloric acid (330 g/l) (0.066 mol.) are added. The clear solution is evaporated in vacuo, the residue is treated with ether and dried at 70° to give 11.0 g. (96%) of N-methyl-2,6-diphenyl-2H-pyrazolo[3,4-b]pyridin-4-amine, hydrochloride (1:1), hydrate (2:1); m.p. 205°–210° (dec.).

EXAMPLE 18

N,N-Diethyl-2,6-diphenyl-2H-pyrazolo[3,4-b]pyridin-4-amine, hydrochloride (1:1)

By substituting diethylamine for methylamine in the procedure of Example 17, N,N-diethyl-2,6-diphenyl-2H-pyrazolo[3,4-b]pyridin-4-amine is obtained; yield 81%; m.p. 148°–149° (ethyl acetate/hexane 1:3).

To 11.3 g. of the amine (0.033 mol.) dissolved in 70 ml. of chloroform, 7.3 ml. of ethereal hydrochloric acid (330 g/l) (0.066 mol.) and 30 ml. of ether are added. After standing overnight, the hydrochloride of N,N-diethyl-2,6-diphenyl-2H-pyrazolo[3,4-b]pyridin-4-amine is filtered off, washed with ether and dried at 40°, yield: 13.5 g. (74%); m.p. 120°–126° (dec.).

The following additional products are produced by the procedure of the Example indicated:

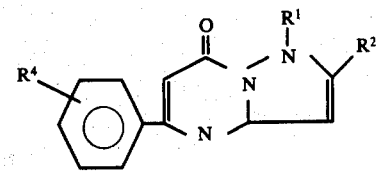

| Ex. | $R^1$ | $R^2$ | $R^4$ | Procedure of Ex. |
|---|---|---|---|---|
| 19 | $C_2H_5$ | H | 3-Br | 1a |
| 20 | C₆H₅– | $CH_3$ | H | 15 |
| 21 | C₆H₅–CH₂CH₂– | H | $NH_2$ | 15 |
| 22 | C₆H₅–CH₂– | $CH_3$ | OH | 15 |
| 23 | cyclopentyl | H | H | 1a |
| 24 | cyclohexyl | H | H | 1a |
| 25 | $CH_3$ | C₆H₅– | 4-Cl | 1a |
| 26 | $C_2H_5$ | $C_2H_5$ | $CH_3O-$ | 10 |
| 27 | cyclobutyl | H | H | 1a |
| 28 | $C_4H_9$ | $CH_3$ | H | 1a |

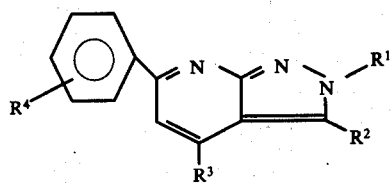

| Example | $R^1$ | $R^2$ | $R^3$ | $R^4$ | Procedure of Example |
|---|---|---|---|---|---|
| 29 | $C_2H_5$ | H | –N(piperazin-1-yl)NH | 3-Br | 7 |

-continued

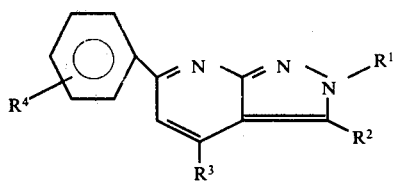

| Example | R¹ | R² | R³ | R⁴ | Procedure of Example |
|---|---|---|---|---|---|
| 30 | phenyl | CH₃ | —OCH₃ | H | 9 |
| 31 | —CH₂CH₂—phenyl | H | —NH(C₃H₇) | NH₂ | 4 |
| 32 | phenyl—CH₂— | CH₃ | —N(piperidinyl) | OH | 7 |
| 33 | cyclopentyl | H | —N(C₂H₅)₂ | H | 13 |
| 34 | CH₃ | phenyl | —OC₂H₅ | 4-Cl | 9 |
| 35 | C₂H₅ | C₂H₅ | —NHCH₃ | 4-CH₃O— | 3 |
| 36 | cyclobutyl | H | —N(CH₃)₂ | H | 6 |
| 37 | C₄H₉ | CH₃ | —OC₄H₉ | H | 8 |
| 38 | C₂H₅ | H | —N(N'-methylpiperazinyl) | 4-OH | 7 |
| 39 | CH₃ | CH₃ | —N(N'-(2-hydroxyethyl)piperazinyl) | H | 7 |
| 40 | CH₃ | H | —N(4-methylpiperidinyl) | 3-NH₂ | 7 |
| 41 | C₂H₅ | CH₃ | —N(2-methylpiperidinyl) | H | 7 |
| 42 | phenyl—CH₂— | H | —N(piperazinyl)NH | H | 7 |

-continued

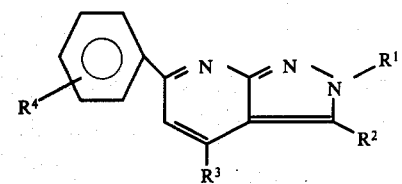

| Example | R¹ | R² | R³ | R⁴ | Procedure of Example |
|---|---|---|---|---|---|
| 43 | $C_2H_5$ | phenyl | —N(piperidinyl) | OH | 7 |
| 44 | $CH_3$ | phenyl | —$OC_4H_9$ | H | 8 |
| 45 | $CH_3$ | phenyl | —N(pyrrolidinyl) | $CH_3O$— | 7 |

What is claimed is:

1. A compound of the formula

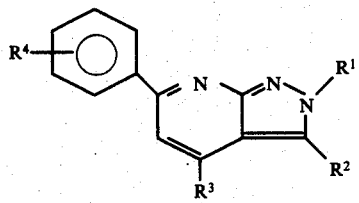

wherein
R¹ is lower alkyl, phenyl, phenyl-lower alkyl or cyclo-lower alkyl;
R² is hydrogen, lower alkyl or phenyl;
R³ is lower alkylamino or di(lower alkylamino);
R⁴ is hydrogen, halogen, hydroxy, lower alkoxy or amino; and physiologically acceptable acid addition salts thereof.

2. A compound as in claim 1 wherein R¹ is lower alkyl or phenyl; R² is hydrogen; R³ is lower alkylamino or di(lower alkyl)amino; and R⁴ is hydrogen or halogen; and physiologically acceptable acid addition salts thereof.

3. A compound as in claim 1 wherein R³ is lower alkylamino.

4. A compound as in claim 1 wherein R³ is di(lower alkyl)amino.

5. A compound as in claim 1 wherein R² and R⁴ each is hydrogen.

6. A compound as in claim 1 wherein R² is hydrogen and R⁴ is chloro.

7. A compound as in claim 5 wherein R¹ is methyl and R³ is methylamino.

8. A compound as in claim 5 wherein R¹ is methyl and R³ is butylamino.

9. A compound as in claim 5 wherein R¹ is methyl and R³ is diethylamino.

* * * * *